(12) United States Patent
Peschel et al.

(10) Patent No.: US 9,718,751 B2
(45) Date of Patent: Aug. 1, 2017

(54) PROCESS AND PLANT FOR PREPARATION OF ONE OR MORE REACTION PRODUCTS

(71) Applicants: Andreas Peschel, Wolfratshausen (DE); Helmut Fritz, Munich (DE); Thomas Bartesch, Glonn (DE); Johannes Fendt, Munich (DE)

(72) Inventors: Andreas Peschel, Wolfratshausen (DE); Helmut Fritz, Munich (DE); Thomas Bartesch, Glonn (DE); Johannes Fendt, Munich (DE)

(73) Assignee: Linde Aktiengesellschaft, Munich (DE)

( * ) Notice: Subject to any disclaimer, the term of this patent is extended or adjusted under 35 U.S.C. 154(b) by 0 days.

(21) Appl. No.: 14/933,535

(22) Filed: Nov. 5, 2015

(65) Prior Publication Data

US 2016/0130204 A1 May 12, 2016

(30) Foreign Application Priority Data

Nov. 12, 2014 (DE) .................. 10 2014 016 704

(51) Int. Cl.
*C07C 41/01* (2006.01)
*C07C 41/09* (2006.01)
(Continued)

(52) U.S. Cl.
CPC .............. *C07C 41/01* (2013.01); *C01B 3/36* (2013.01); *C07C 41/09* (2013.01);
(Continued)

(58) Field of Classification Search
CPC ........ C07C 41/09; C07C 41/01; C07C 43/043; C01B 3/36; C01B 2203/0233;
(Continued)

(56) References Cited

U.S. PATENT DOCUMENTS

| 7,485,767 B2 | 2/2009 | Lattner et al. |
| 2007/0004809 A1* | 1/2007 | Lattner .................. C01B 3/382 518/700 |

(Continued)

FOREIGN PATENT DOCUMENTS

| DE | 2 362 944 | 12/1973 |
| DE | 2362944 A1 | 7/1974 |

(Continued)

*Primary Examiner* — Jafar Parsa
(74) *Attorney, Agent, or Firm* — Philip H. Von Neida

(57) ABSTRACT

A process for preparing one or more reaction products, in which a first methane-rich feed stream is subjected to a partial oxidation process and/or an autothermal reforming process and a second methane-rich feed stream is subjected to a steam reforming process, in which a first synthesis gas-containing output stream is formed from the first methane-rich feed stream and a second synthesis gas-containing output stream is formed from the second methane-rich feed stream and these synthesis gas streams are used to form a collective synthesis gas stream and fluid from the collective synthesis gas stream is subjected to a molecular weight-increasing reaction in a synthesis feed stream to obtain a synthesis output stream comprising carbon dioxide and the reaction product(s). At least one carbon dioxide-rich first recycle stream is formed from fluid from the synthesis output stream and fluid from the first recycle stream is subjected to the steam reforming process.

16 Claims, 1 Drawing Sheet

(51) Int. Cl.
*C01B 3/36* (2006.01)
*C07C 43/04* (2006.01)

(52) U.S. Cl.
CPC ............... *C01B 2203/025* (2013.01); *C01B 2203/0233* (2013.01); *C01B 2203/0244* (2013.01); *C01B 2203/06* (2013.01); *C01B 2203/1241* (2013.01); *C01B 2203/141* (2013.01); *C01B 2203/148* (2013.01); *Y02P 20/129* (2015.11)

(58) Field of Classification Search
CPC ...... C01B 2203/2203; C01B 2203/025; C01B 2203/141; C01B 2203/148; C01B 2203/0244; C01B 2203/06; C01B 1203/1241
See application file for complete search history.

(56) References Cited

U.S. PATENT DOCUMENTS

2009/0105356 A1    4/2009  Bormann et al.
2015/0018592 A1*  1/2015  Schödel .................. C01B 3/34
                                                   585/639

FOREIGN PATENT DOCUMENTS

| DE | 102012001811 A1 | 8/2013 |
| EP | 0 522 744 A2 | 1/1993 |
| WO | WO 93/15999 | 8/1993 |
| WO | WO 02/26677 A2 | 4/2002 |
| WO | WO 2011/018233 A1 | 2/2011 |

\* cited by examiner

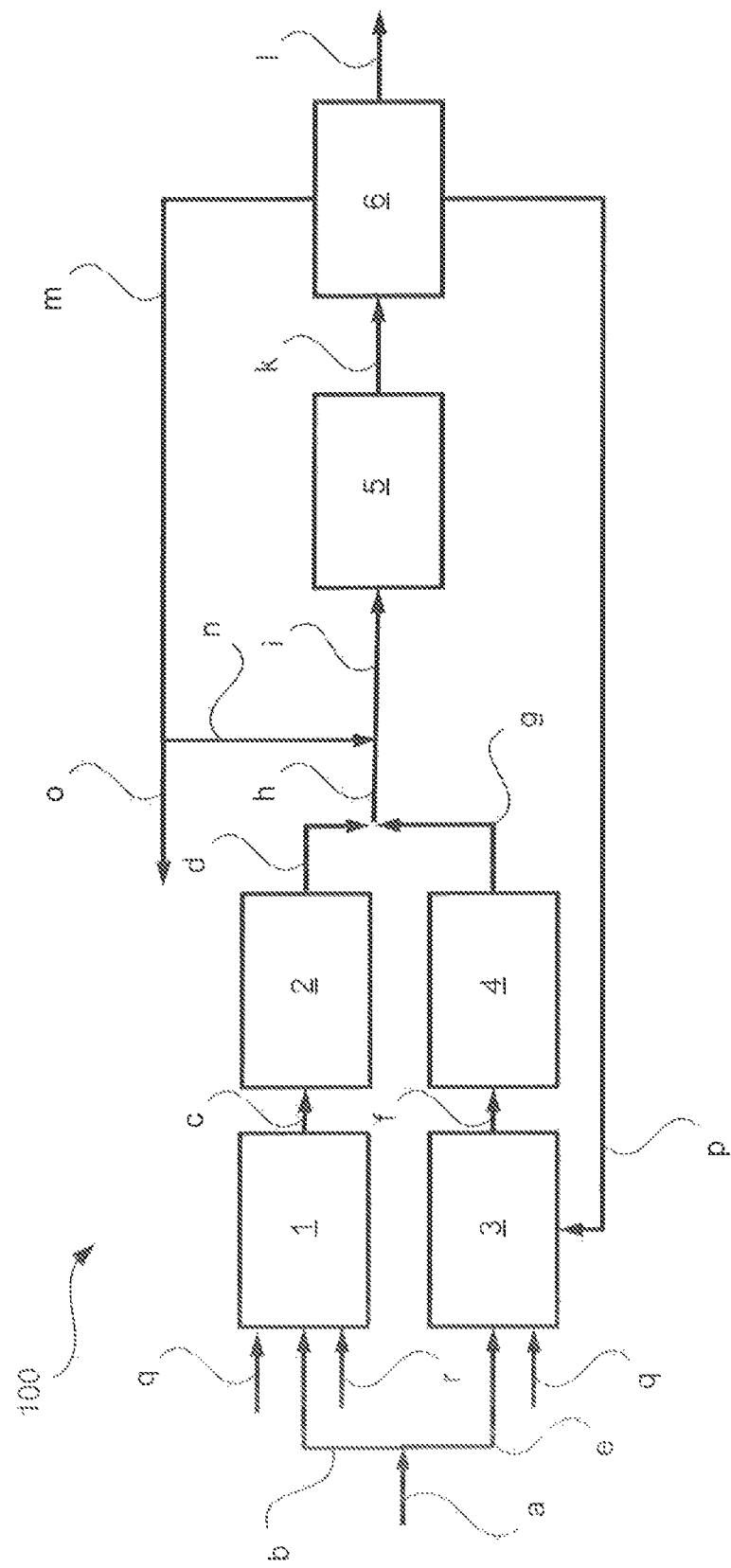

PROCESS AND PLANT FOR PREPARATION OF ONE OR MORE REACTION PRODUCTS

CROSS REFERENCE TO RELATED APPLICATIONS

The present application claims priority from German Patent Application DE 10 2014 016 704.6 filed in the German Patent Office on Nov. 12, 2014.

BACKGROUND OF THE INVENTION

The invention relates to a process and a plant for preparation of one or more reaction products, especially dimethyl ether or other oxygenates, in which a first methane-rich feed stream is subjected to a partial oxidation process and/or an autothermal reforming process and a second methane-rich feed stream is subjected to a steam reforming process, and in which a first synthesis gas-containing output stream is formed by means of the partial oxidation process and/or the autothermal reforming process and a second synthesis gas-containing output stream is formed by means of the steam reforming process, where synthesis gas from the first output stream and synthesis gas from the second output stream are used to form a collective synthesis gas stream and fluid from the collective synthesis gas stream is subjected to a molecular weight-increasing reaction in a synthesis feed stream to obtain a synthesis output stream comprising carbon dioxide and the reaction product(s), characterized in that at least one carbon dioxide-rich first recycle stream is formed from fluid from the synthesis output stream, and in that fluid from the first recycle stream is subjected to the steam reforming process.

PRIOR ART

Dimethyl ether (DME) is the structurally simplest ether. Dimethyl ether contains two methyl groups as organic radicals. Dimethyl ether is polar and conventionally finds use in liquid form as solvent. Dimethyl ether can additionally be used as coolant and hence replace conventional hydrochlorofluorocarbons. As of recently, dimethyl ether is increasingly also being used as a replacement for fuel gas (liquefied gas) and conventional fuels such as diesel. Because of its comparatively high cetane number of 55 to 60, conventional diesel engines, for example, need be modified only slightly, if at all, for operation with dimethyl ether. Dimethyl ether burns comparatively cleanly and without forming soot.

Dimethyl ether can be prepared by means of a two-stage synthesis from synthesis gas via the methanol intermediate, as described, for example, in Chapter 4 of the DME Handbook, Japan DME Forum, Tokyo 2007, ISBN 978-4-0903630-0-9. It is a feature of a "two-stage" synthesis that methanol is first prepared from synthesis gas, by separating the methanol from unconverted synthesis gas and then separately dehydrating the methanol in a further step to give dimethyl ether and water.

The present invention is suitable for use in the preparation of dimethyl ether, but also other oxygenates, from synthesis gas. The synthesis gas or a corresponding collective synthesis gas stream can, in the context of the present invention, be subjected to any desired known molecular weight-increasing reactions, for example the Fischer-Tropsch synthesis.

According to a standard definition, which is also applied here, oxygenates are compounds having at least one alkyl group bonded covalently to an oxygen atom. The at least one alkyl group may have up to five, up to four or up to three carbon atoms. More particularly, the oxygenates that are of interest in the context of the present invention have alkyl groups having one or two carbon atoms, especially methyl groups. More particularly, they are monohydric alcohols and dialkyl ethers such as methanol and dimethyl ether or corresponding mixtures.

As early as 1973, the patent literature, for example DE 236 29 44 A1, described the direct synthesis of dimethyl ether from synthesis gas. In this case, a combined reaction stage is used, in which methanol and dimethyl ether are formed from hydrogen, carbon monoxide and carbon dioxide. It is a feature of the "direct" synthesis of dimethyl ether from synthesis gas that there is typically no separation of methanol and separate further conversion thereof to dimethyl ether. Corresponding methods can be found, for example, in the publication "Dimethyl Ether (DME) Technology and Markets", PERP07/08-S3 from Nexant Technology, Inc., December 2008, and the DME Handbook from the Japan DME Forum that has been mentioned.

The stoichiometric number (SN) is standard in the specialist field for characterization of synthesis gas. It is defined as $$SN=(xH_2-xCO_2)/(xCO+xCO_2),$$

where x in each case is the molar content of the hydrogen ($H_2$), carbon monoxide (CO) and carbon dioxide ($CO_2$) components. In corresponding two-stage syntheses, synthesis gases having stoichiometric numbers of 2 to 2.05 are typically used as fresh feed (makeup) for the methanol synthesis; in direct syntheses, in contrast, much smaller stoichiometric numbers are often used.

In the conventional processes for one-stage synthesis of dimethyl ether, for example, stoichiometric numbers of 1 to 1.5 are required, and it is generally the case that the performance of a corresponding process should be preceded by separation of carbon dioxide from the synthesis gas. A process developed by the applicant in which dimethyl ether is synthesized directly from methane-rich natural gas, in contrast, embraces the use of a synthesis gas having a stoichiometric number of 2 to 5. This can be achieved, for example, by a fresh feed (makeup) of synthesis gas having a stoichiometric number of about 2.05 and recycling of synthesis gas unconverted in each case, which results in enrichment of hydrogen in the process and hence an increase in the stoichiometric number. Said stoichiometric number of 2 to 5 is obtained here at the inlet into the synthesis reactor used.

There are different known methods of providing a synthesis gas having a stoichiometric number of 2 to 2.05 from methane-rich natural gas. For example, US 2009/0105356 A1 proposes producing a synthesis gas by a combination of a steam reforming and an autothermal reforming connected in series, with feeding of a portion of the feed directly to the autothermal reforming, bypassing the steam reforming. For example, U.S. Pat. No. 7,485,767 B2 discloses a method in which natural gas is sent to a partial oxidation or an autothermal reforming on the one hand and to a steam reforming on the other hand. The partial oxidation or autothermal reforming on the one hand and the steam reforming on the other hand are thus arranged in parallel. The respective synthesis gases obtained are combined to give a collective synthesis gas stream having the desired stoichiometric number.

The partial oxidation or the autothermal reforming here is conducted at a higher pressure than the steam reforming, and so the synthesis gas obtained in the steam reforming has to be recompressed before being combined with the synthesis gas present in the partial oxidation or the autothermal reforming. Alternative processes are also known and are described, for example, in WO 1993/015999 A1 and EP 0 522 744 A2.

Process calculations suggest that particularly a parallel connection of partial oxidation or autothermal reforming on the one hand and steam reforming on the other hand will lead to particularly high energy efficiency. Energy efficiency is enhanced especially when the partial oxidation or autothermal reforming on the one hand is conducted at comparatively high pressure (for example 35 to 80 bar) and the steam reforming on the other hand at comparatively low pressure (for example about 10 to 35 bar).

In the direct synthesis of dimethyl ether, if unconverted synthesis gas is recycled to the synthesis, a high carbon dioxide concentration builds up in the synthesis gas. This can lead to reduced reaction rates and lower conversion. In addition, the direct synthesis of dimethyl ether can give rise to comparatively large amounts of by-products such as methane, ethane and propane, which have to be removed in a costly and inconvenient manner. The situation is similar for other molecular weight-increasing reactions.

The problem addressed by the present invention is that of improving corresponding processes, especially with regard to the latter aspects.

SUMMARY OF THE INVENTION

The problem is solved by a process and a plant for preparation of one or more reaction products, especially dimethyl ether or other oxygenates, as described herein.

Before the features and advantages of the present invention are described, the fundamentals thereof and the terms used will be discussed below.

With regard to processes and apparatuses for preparation of synthesis gas, especially in terms of partial oxidation, autothermal reforming (ATR) and steam methane reforming (SMR), reference is made to relevant textbook articles, for example the "Gas Production" article in Ullmann's Encyclopedia of Industrial Chemistry, online edition, 15 Dec. 2006, DOI 10.1002/14356007.a12_169.pub2, or section 4.2, "Synthesis gas production technology", in the DME Handbook.

The present application uses the terms "pressure level" and "temperature level" to characterize pressures and temperatures, which is supposed to express the fact that corresponding pressures and temperatures in a corresponding plant need not be used in the form of exact pressure and temperature values, in order to realize the inventive concept. However, such pressures and temperatures typically vary within particular ranges which are, for example, ±1%, 5%, 10%, 20% or even 50% about a mean value. Corresponding pressure levels and temperature levels may be in distinct ranges or in ranges which overlap one another. More particularly, for example, pressure levels include unavoidable or expected pressure drops, for example owing to cooling effects. The same applies to temperature levels. The pressure levels reported here in bar are absolute pressures.

In the terminology used here, liquid and gaseous streams may be rich or poor in one or more components, where "rich" may mean a content of at least 50%, 75%, 90%, 95%, 99%, 99.5%, 99.9% or 99.99% and "poor" may mean a content of at most 50%, 25%, 10%, 5%, 1%, 0.1% or 0.01%, on a molar, weight or volume basis. The term "predominantly" may correspond to the definition of "rich". In the terminology used here, liquid and gaseous streams may also be enriched in or depleted of one or more components, these terms relating to a corresponding content in the starting mixture from which the liquid or gaseous stream has been obtained. The liquid or gaseous stream is "enriched" when it contains at least 1.1 times, 1.5 times, 2 times, 5 times, 10 times, 100 times or 1000 times the content, and "depleted" when it contains at most 0.9 times, 0.5 times, 0.1 times, 0.01 times or 0.001 times the content, of a corresponding component, based on the starting mixture.

If it is said here that a stream is formed "from fluid" in another stream, this is understood to mean that all the fluid from the starting stream is used to form the further stream, but it is also possible that only a portion of a corresponding starting stream is used, for example after removal of other components, for example of condensates.

A "compressor" in the terminology used here is an apparatus which is set up to compress at least one gaseous stream from at least one feed pressure at which it is supplied to the compressor to at least one final pressure at which it is withdrawn from the compressor. A compressor constitutes one construction unit, but may have two or more "compressor stages" in the form of piston, screw and/or impeller or turbine arrangements (i.e. axial or radial compressor stages). More particularly, corresponding compressor stages are driven by means of a common drive, for example via a common shaft.

Advantages of the Invention

At the inlet of a reactor for conversion of the synthesis gas, i.e. for performance of a molecular weight-increasing reaction as elucidated above, a stoichiometric number of 2 or more than 2 is found to be advantageous. The above-elucidated conventional methods for direct synthesis of dimethyl ether work with synthesis gases in which the ratio of hydrogen to carbon monoxide is 1 and which typically include no or barely any carbon dioxide. As a result, there is a very high conversion therein, but comparatively large amounts of carbon dioxide are also formed. The formation of carbon dioxide worsens the energy efficiency and emission characteristics of corresponding plants.

As has been recognized in accordance with the invention, a small proportion of carbon dioxide is advantageous because this enables, for example, a higher conversion in the reactor. This is at first unexpected in thermodynamic terms, since the highest conversion thermodynamically possible is with a carbon dioxide-free gas. However, faster reaction kinetics in the presence of carbon dioxide result in an increase in the conversion in the reactor. Therefore, it is particularly important to accurately set the proportion of carbon dioxide at the reactor inlet. For this purpose, and in order to achieve a desired stoichiometric number of 2, for example, a combination of partial oxidation or autothermal reforming and SMR is particularly efficient.

In addition, the formation of inert components having boiling points between dimethyl ether (or another oxygenate or reaction product formed in the synthesis gas conversion) and carbon dioxide is avoided in the synthesis gas circuit around a corresponding reactor, since these components are likewise recycled into the steam reforming and are converted to synthesis gas therein.

The present invention therefore proposes a process for preparing one or more reaction products of a molecular weight-increasing reaction, for example dimethyl ether or other oxygenates, in which a first methane-rich feed stream is subjected to a partial oxidation process and/or an autothermal reforming process and a second methane-rich feed stream is subjected to a steam reforming process. In this respect, the process according to the invention is equivalent to that as described previously, for example, with reference to U.S. Pat. No. 7,485,767 B2. Steam reforming may especially include a pre-reforming. As known in this respect, a first synthesis gas-containing output stream is formed by means of the partial oxidation process and/or the autothermal reforming process, and a second synthesis gas-containing output stream is formed by means of the steam reforming process. If it is said here that a "synthesis gas-containing" output stream is formed, this is understood to mean that an output stream including hydrogen, carbon dioxide and carbon monoxide in the proportions typically encountered in synthesis gas is formed. These proportions can, as elucidated above, be defined conveniently via the stoichiometric number.

The invention further envisages forming a collective synthesis gas stream from synthesis gas from the first output stream and synthesis gas from the second output stream and subjecting fluid from the collective synthesis gas stream to a molecular weight-increasing reaction, for example the direct synthesis of dimethyl ether, in a synthesis gas feed stream to obtain a synthesis output stream comprising carbon dioxide and at least one reaction product. The compounds present in the synthesis output stream obtained are partly formed in the molecular weight-increasing reaction, for example the process for direct synthesis of dimethyl ether, and are partly unconverted compounds from the synthesis feed stream.

As explained above, a direct synthesis of dimethyl ether is a synthesis in which no methanol is obtained separately and converted further to dimethyl ether; instead, dimethyl ether and possibly methanol are formed directly in a single reaction step. A "reaction step" should not be regarded as a molecular reaction step but as a technical reaction step. R is a feature of this technical reaction step that it is conducted without removal of intermediates in one or more reactors, but may include several molecular reaction steps. The synthesis output stream in the direct synthesis of dimethyl ether contains not only the carbon dioxide and dimethyl ether components mentioned but also methanol, unconverted synthesis gas and by-products of the dimethyl ether synthesis, as elucidated above, especially hydrocarbons and inert gases such as methane, ethane and nitrogen. Corresponding compounds can also be obtained in other molecular weight-increasing reactions, as elucidated at the outset. A "molecular weight-increasing reaction" is a reaction in which compounds at least partly of higher molecular weight, such as oxygenates or hydrocarbons, are formed from the low molecular weight compounds from the synthesis gas, especially carbon monoxide and hydrogen.

As explained above, in known processes comprising the steps elucidated, it is disadvantageous that, when the unconverted synthesis gas from the synthesis output stream is recycled, carbon dioxide can be enriched in a corresponding process and hence can inhibit the dimethyl ether synthesis or other molecular weight-increasing reactions. The invention therefore envisages forming at least one carbon dioxide-rich first recycle stream from fluid from the synthesis output stream and subjecting fluid from the first recycle stream to the steam reforming process. The withdrawal of the carbon dioxide-rich first recycle stream reduces the carbon dioxide content of the unconverted synthesis gas remaining in the synthesis output stream. The recycling of the carbon dioxide-rich first recycle stream into the steam reforming is particularly favorable because the removal of the carbon dioxide-rich first recycle stream can be effected at a somewhat higher pressure than the steam reforming. The carbon dioxide can therefore be fed to the steam reforming without any separate compression and be converted efficiently to carbon monoxide therein, Overall, this increases the carbon efficiency without an additional compressor and increases the conversion in the molecular weight-increasing reaction.

The remaining synthesis gas, which is likewise removed from the synthesis output stream or is obtained after removal of further components, especially of reaction products of the molecular weight-increasing reaction such as dimethyl ether, has a comparatively low carbon dioxide content because of the measures proposed in accordance with the invention, and so the molecular weight-increasing reaction into which it is conducted can be supplied with a hydrogen-rich and comparatively carbon dioxide-poor synthesis gas in particular. This is formed from the synthesis gas of the collective synthesis gas stream and a corresponding recycle stream.

The invention thus advantageously envisages forming a synthesis gas-containing and carbon dioxide-depleted second recycle stream from fluid from the synthesis output stream, with feeding of fluid from the second recycle stream to the synthesis feed stream. As already explained, the formation of the carbon dioxide-rich first recycle stream can reduce the carbon dioxide contents in a corresponding second recycle stream.

Particular advantages arise when the synthesis gas which is formed as what is called a makeup stream from the synthesis gas from the first output stream and the second output stream has a stoichiometric number of 1.5 to 2. A "makeup stream" is the collective synthesis gas stream from which the synthesis feed stream is formed together with the second recycle stream. This can achieve the effect that the synthesis feed stream has a stoichiometric number of 2 to 3.

The present invention can thus be characterized, according to the embodiment elucidated, in that a parallel connection of partial oxidation or autothermal reforming and steam reforming is undertaken, with recycling of a carbon dioxide rich stream withdrawn from a separation sequence connected downstream of the molecular weight-increasing reaction, for example dimethyl ether synthesis, into the steam reforming as ("first") recycle stream. Said processes, on the basis of the present invention, can provide a synthesis gas having a stoichiometric number of less than 2, whereas fresh synthesis gas typically used in conventional processes is characterized by a stoichiometric number of 2 to 2.05.

In corresponding processes, a product stream enriched at least one reaction product of the molecular weight-increasing reaction, for example dimethyl ether, is advantageously formed from the fluid from the synthesis output stream, as is basically known in molecular weight-increasing reactions, and withdrawn from the process. The present invention especially enables the synthesis of dimethyl ether in a more economically viable manner compared to the prior art, since the decrease in the carbon dioxide content and the setting of a suitable stoichiometric number of the synthesis feed stream give favorable reaction conditions.

A further particularly advantageous aspect of the present invention is that the removal of carbon dioxide from a recycle stream recycled directly into the molecular weight-increasing reaction, for example into the dimethyl ether synthesis, increases the carbon monoxide/carbon dioxide ratio and enhances the reaction conversion. This reduces the volumes that have to be managed in corresponding recycle streams, and allows a reactor for performance of the molecular weight-increasing reaction and a downstream separation section to be executed in a smaller design. The invention simultaneously enables the removal of inert components such as methane and ethane from the process, which can be treated in a suitable manner in the steam reforming.

The first recycle stream is advantageously formed with a content of at least 60, 80 or 90 mole percent of carbon dioxide and for the rest typically includes components having a boiling point below at least one reaction product formed in the molecular weight-increasing reaction, especially below dimethyl ether, for example ethane. The ethane removed can particularly advantageously be utilized in the steam reforming and is present in the first recycle stream. A particular advantage of the present invention here is that carbon dioxide and components such as ethane can be removed from the synthesis output stream in existing separation devices without additional equipment for pressure swing absorption or membrane processes.

The separation of reaction products of the molecular weight-increasing reaction, for example of dimethyl ether, from the synthesis output stream is typically effected by means of absorption or condensation and distillation. In the first case (absorption), physical scrubbing agents such as methanol are used in order to separate the reaction product(s), for example dimethyl ether, from the rest of the synthesis output stream. At the same time, a certain amount of carbon dioxide also dissolves in the scrubbing agent and has to be removed again from the reaction product(s) after the scrubbing agent has been regenerated. In the second case (condensation and distillation), the synthesis output stream is cooled down to a temperature at which the reaction product(s), for example dimethyl ether, and heavier components condense out. At the same time, a portion of the carbon dioxide also condenses. The condensate obtained in this way is separated by distillation, giving rise to the carbon dioxide-rich first recycle stream without an additional separation unit. In both cases, this also contains other comparatively light compounds. The two processes can also be combined. What they have in common is that the purification of the reaction product(s), for example dimethyl ether, requires a column which separates carbon dioxide from the reaction product(s). This column may advantageously be operated between 10 and 30 bar, such that, as explained, corresponding components can be conducted into the steam reforming without additional compression.

Components such as ethane are thus removed from the synthesis gas loop around the reactor for performance of the molecular weight-increasing reaction and converted to synthesis gas in the steam reforming. It is customarily the case that these components are inert in the synthesis gas loop around the reactor and thus reduce the partial pressure of the reactants. This reduces the conversion and additionally increases the volume flow rates in the entire synthesis gas loop around the reactor, which has adverse effects.

Particularly advantageously, the first recycle stream is provided at a pressure of about 10 to 30 bar, and so, as also explained hereinafter, has a suitable pressure to be recyclable directly into the steam reforming process without additional compression.

Advantageously, the second recycle stream comprises predominantly hydrogen, carbon dioxide and carbon monoxide, where the carbon dioxide content is 1 to 15 mole percent, and can thus be much lower than that of conventional recycle streams which are recycled into the synthesis stage in known processes for synthesis of dimethyl ether.

According to a particularly preferred configuration of the process of the invention, the first output stream is provided at a first pressure level and the second output stream at a second pressure level lower than the first pressure level, the formation of the collective synthesis gas stream being preceded by compression of the synthesis gas from the second output stream to the first pressure level. In this connection, the above-elucidated pressure levels are particularly advantageous, the first pressure level being especially 30 to 100 bar, advantageously 35 to 80 bar, and the second pressure level especially 5 to 40 bar, advantageously 10 to 35 bar. Said pressure levels enable particularly advantageous reaction conditions; at the same time, operation of the steam reforming process at the second pressure level allows simple recycling of the first recycle stream without additional apparatus.

Advantageously, in the context of the process of the invention, the first feed stream and the second feed stream are formed from fluid in a common starting stream, for example from a natural gas stream which is provided at the first and second pressure levels and is previously or subsequently heated and desulfurized. The joint formation of the first and second feed streams by heating and desulfurization enables a particularly efficient process. Advantageously, heating is accomplished using waste heat from the second output stream, i.e. the output stream from the steam reforming.

The present invention further relates to a plant for preparing one or more reaction products, especially dimethyl ether or other oxygenates having means of subjecting a first methane-rich feed stream to a partial oxidation process and/or an autothermal reforming process and a second methane-rich feed stream to a steam reforming process, and having means of forming a first synthesis gas-containing output stream by means of the partial oxidation process and/or the autothermal reforming process and a second synthesis gas-containing output stream by means of the steam reforming process, with provision of means of forming a collective synthesis gas stream from synthesis gas from the first output stream and the second output stream and subjecting fluid from the collective synthesis gas stream to a molecular weight-increasing reaction in a synthesis feed stream to obtain a synthesis output stream comprising carbon dioxide and dimethyl ether, characterized by means of forming at least one carbon dioxide-rich first recycle stream from fluid from the synthesis output stream and of subjecting fluid from the first recycle stream to the steam reforming process. The plant is advantageously capable of performing a process as elucidated above and has corresponding means for the purpose. With regard to features and advantages, reference is made explicitly to the above details.

BRIEF DESCRIPTION OF THE DRAWINGS

The invention is described in detail hereinafter with reference to the appended FIGURE, which shows a preferred embodiment of the invention.

The FIGURE illustrates a plant according to one embodiment of the invention in the form of a schematic flow diagram.

DETAILED DESCRIPTION OF THE INVENTION

The FIGURE shows a plant according to one embodiment of the invention in the form of a schematic flow diagram with the overall reference 100. The FIGURE simultaneously illustrates steps of a corresponding process, and so, when reference is made to a "partial oxidation" or "autothermal reforming", "steam reforming", "synthesis gas provision", etc., or to a "process for synthesizing dimethyl ether", corresponding plant components, for example reactors, but also corresponding process steps, may be embraced. The steam reforming or one or more corresponding reactors may especially embrace a pre-reforming or corresponding reactor units.

The plant 100 is supplied with a starting stream a, for example heated and/or desulfurized natural gas. Fluid from starting stream a may be provided, for example, at a first and a second pressure level at which the latter is supplied to a partial oxidation or autothermal reforming 1 on the one hand and a steam reforming 3 on the other hand (see below), with combined or separate heating and desulfurization before or after the provision at appropriate pressure levels. The heating can be effected, for example, by means of waste heat from the steam reforming 3 or a stream obtained in a corresponding manner.

From fluid from the starting stream a, a first feed stream b at a pressure level of, for example, 30 to 100 bar ("first" pressure level) is fed to the partial oxidation or autothermal reforming 1. The partial oxidation or autothermal reforming 1 is also supplied with a vapor stream q and an oxygen stream or oxygen-rich stream r. By means of the partial oxidation or autothermal reforming 1, an output stream c ("first" output stream) is obtained and fed to a synthesis gas processing 2. The synthesis gas processing 2 may comprise, for example, a scrubber. Downstream of the synthesis gas processing 2, a first synthesis gas stream d is present at the first pressure level elucidated above.

A second feed stream e formed from the fluid from the starting stream a is fed to the steam reforming 3, which is additionally supplied with a vapor stream q and a recycle stream ("first" recycle stream) p elucidated below. The steam reforming 3 affords an output stream f ("second" output stream) which is likewise fed to a synthesis gas processing, referred to as 4 here. Downstream of the synthesis gas processing 4, a synthesis gas stream g ("second" synthesis gas stream) is present.

The second synthesis gas stream g typically has a lower pressure than the first synthesis gas stream d because the steam reforming 3, as elucidated above, is typically operated at a lower pressure level (the "second" pressure level). The second synthesis gas stream g is therefore compressed (not shown). The synthesis gas streams d and g, or even only certain proportions of corresponding synthesis gas streams d and g, are subsequently combined to give a collective synthesis gas stream h. Also fed into the collective synthesis gas stream h is a recycle stream ("second" recycle stream") n which is elucidated below, forming a synthesis feed stream i.

The synthesis feed stream i is fed to a molecular weight-increasing reaction 5, for example for direct synthesis of dimethyl ether, by means of which a synthesis output stream k is obtained, which, as mentioned, as well as the target product(s), for example dimethyl ether, comprises unconverted synthesis gas and further by-products, for example methanol, nitrogen, methane and ethane. The synthesis output stream k or fluid in a corresponding synthesis output stream k is fed to a separation unit 6 in which one of the streams obtained is a stream l rich in one or more reaction products of the molecular weight-increasing reaction 5, for example dimethyl ether, as the product stream, which is discharged from a corresponding process.

Also formed in the separation unit 6 are the first recycle stream p mentioned and a further stream m. The first recycle stream p, as mentioned, is rich in carbon dioxide and especially includes 60 to 100 mole percent of carbon dioxide. Also transferred into the first recycle stream p are inert gases, for example ethane, having a vapor pressure below the at least one reaction product, for example dimethyl ether. This first recycle stream p is recycled into the steam reforming 3. It has a pressure of typically about 10 to 30 bar, and so it can be recycled into the steam reforming 3 without further compression. Any remaining unconverted synthesis gas in the form of stream m is depleted of carbon dioxide by the formation of the first recycle stream p. Stream m is transferred into a processing unit (not shown) in which a stream n, the second recycle stream mentioned, is formed with removal of a stream o which may especially comprise light inert components such as methane or hydrogen, for example by purging. Stream n is optionally recompressed, in order that it attains the pressure level of the collective synthesis gas stream h, optionally also in a compressor which is used for the compression of the second synthesis gas stream g, or corresponding compressor stages.

Through the use of the process of the invention, it is possible to produce the collective synthesis gas stream h with a stoichiometric number of less than 2 and the synthesis feed stream i with a stoichiometric number with greater than 2 and a simultaneously low carbon dioxide content. Alternatively, provision with a stoichiometric number of more than 2 is possible.

The invention is also suitable, in addition to the embodiments described, for recycling of a methanol fraction from a separation unit 6 into the molecular weight-increasing reaction 5. Further streams may occur in a separation unit 6 or other separation units not illustrated, for example water-rich streams. As well as the first recycle stream p, it is also possible to supply external carbon dioxide-rich streams to the steam reforming 3. Such "external" carbon dioxide can be separated, for example, from natural gas which is used as feed stream a. Corresponding carbon dioxide may also remain in a starting stream a which is used for formation of the feed streams b and e, and therefore be fed to the partial oxidation or autothermal reforming 1 and/or the steam reforming 3.

Since it is hydrogen- and methane-rich, the stream o elucidated may be used, for example, as fuel gas; portions thereof may also be recycled into the steam reforming or partial oxidation 1 into which starting stream a is fed, or recycled to a prereformer (not shown). In this way, the energy efficiency of a corresponding plant can be increased further. It is also possible to obtain hydrogen, for example for desulfurization and/or export from the stream o. The first recycle stream p can also be recycled partly to a synthesis gas compressor, likewise not shown in the FIGURE. Likewise possible is recycling to a further upstream reactor, for example a shift reactor or prereformer. It is also possible to recycle corresponding streams to one or more heat exchangers.

What we claim is:

1. A process for preparing one or more reaction products, in which a first methane-rich feed stream is subjected to a partial oxidation process and/or an autothermal reforming process and a second methane-rich feed stream is subjected to a steam reforming process, and in which a first synthesis gas-containing output stream is formed by means of the partial oxidation process and/or the autothermal reforming process and a second synthesis gas-containing output stream is formed by means of the steam reforming process, where synthesis gas from the first output stream and synthesis gas from the second output stream are used to form a collective synthesis gas stream and fluid from the collective synthesis gas stream is subjected to a molecular weight-increasing reaction in a synthesis feed stream to obtain a synthesis output stream comprising carbon dioxide and the reaction products from which at least one carbon dioxide-rich first recycle stream and a synthesis gas-containing and carbon dioxide-depleted second recycle stream are formed, whereby fluid from the first recycle stream is subjected to the steam reforming process and fluid from the second recycle stream is used in the formation of the synthesis feed stream, characterized in that the collective synthesis gas stream has a stoichiometric number of 1.5 to 2.05 and/or the synthesis feed stream has a stoichiometric number of 2 to 5 and that the carbon dioxide-rich first recycle stream is obtained from synthesis output stream by condensation and distillation.

2. The process according to claim 1, in which a product stream enriched in the reaction products is formed from fluid from the synthesis output stream and withdrawn from the process.

3. The process according to claim 1, in which the first recycle stream has a content of at least 60 mole percent of carbon dioxide and the remainder comprises predominantly components having boiling points below that of the reaction products.

4. The process according to claim 1, in which the first recycle stream is provided at a pressure of 5 to 40 bar.

5. The process according to claim 1, in which the second recycle stream comprises predominantly hydrogen, carbon dioxide and carbon monoxide, where the carbon dioxide content is from 0 to 20 mole percent.

6. The process according to claim 1, in which the first output stream is provided at a first pressure level and the second output stream at a second pressure level lower than the first pressure level, the formation of the collective synthesis gas stream being preceded by compression of the synthesis gas from the second output stream to the first pressure level.

7. The process according to claim 6, in which the first pressure level is at 30 to 100 bar and the second pressure level at 5 to 40 bar.

8. The process according to claim 6, in which the first feed stream and the second feed stream are formed from fluid in a starting stream which is provided at the first and second pressure levels and is previously or subsequently heated and desulfurized.

9. The process according to claim 8, in which the fluid from the starting stream is heated using waste heat from the first output stream, from the second output stream and/or from the collective synthesis gas stream.

10. The process according to claim 1, in which the molecular weight-increasing reaction comprises the synthesis of dimethyl ether and the reaction product(s) comprises dimethyl ether.

11. The process according to claim 3, in which the first recycle stream consists exclusively of carbon dioxide.

12. The process according to claim 3, in which the first recycle stream has a content selected from the group consisting of at least 70 mole percent of carbon dioxide and the remainder comprises predominantly components having boiling points below that of the reaction products.

13. The process according to claim 4, in which the first recycle stream is provided at a pressure of 10 to 30 bar.

14. The process according to claim 5, wherein the carbon dioxide content is from 3 to 15 mole percent.

15. The process according to claim 7, in which the first pressure level is at 35 to 80 bar and the second pressure level is at 10 to 35 bar.

16. The process according to claim 1, wherein the synthesis is the direct synthesis.

* * * * *